(12) United States Patent
Yu et al.

(10) Patent No.: US 8,889,149 B2
(45) Date of Patent: Nov. 18, 2014

(54) USE OF FLAGELLIN TO PREVENT AND TREAT GRAM NEGATIVE BACTERIAL INFECTION

(75) Inventors: Fu-shin X. Yu, Troy, MI (US); Ashok Kumar, Detroit, MI (US); Jing Zhang, Northville, MI (US); Linda D. Hazlett, Grosse Point, MI (US); Jia Yin, Warren, MI (US)

(73) Assignee: Wayne State University, Detroit, MI (US)

( * ) Notice: Subject to any disclaimer, the term of this patent is extended or adjusted under 35 U.S.C. 154(b) by 598 days.

(21) Appl. No.: 12/279,671

(22) PCT Filed: Feb. 15, 2007

(86) PCT No.: PCT/US2007/062255
§ 371 (c)(1),
(2), (4) Date: Aug. 15, 2008

(87) PCT Pub. No.: WO2007/098371
PCT Pub. Date: Aug. 30, 2007

(65) Prior Publication Data
US 2010/0104516 A1    Apr. 29, 2010

Related U.S. Application Data

(60) Provisional application No. 60/773,919, filed on Feb. 16, 2006.

(51) Int. Cl.
*A61K 39/02* (2006.01)
*A61K 38/16* (2006.01)

(52) U.S. Cl.
CPC ................................... *A61K 38/164* (2013.01)
USPC .......................................... 424/234.1; 530/350

(58) Field of Classification Search
None
See application file for complete search history.

(56) References Cited

U.S. PATENT DOCUMENTS

2003/0044429 A1    3/2003    Aderem et al.

OTHER PUBLICATIONS

Mizel, Steven B. and Snipes, James A, "Gram-Negative Flagellin-induced Self-tolerance Is Associated with a Block in Interleukin-1 Receptor-associated Kinase Release from Toll-like Receptor 5," The Journal of Biological Chemistry 277(25), pp. 22414-22420, 2002.

*Primary Examiner* — Jennifer Graser
(74) *Attorney, Agent, or Firm* — Lee & Hayes, PLLC; C. Rachal Winger

(57) ABSTRACT

The disclosure describes use of flagellin polypeptides to induce tolerance to gram negative bacteria, such as *Pseudomonas aeruginosa*, in order to alleviate the effects of the inflammatory response to bacterial infection in a patient. Also described are methods and compositions for treating and preventing keratitis, cystic fibrosis, asthma, and other diseases and conditions in which inflammation contributes to the pathology and symptoms.

9 Claims, 11 Drawing Sheets

FIGURE 5A, 5B, 5C, and 5D

USE OF FLAGELLIN TO PREVENT AND TREAT GRAM NEGATIVE BACTERIAL INFECTION

CROSS-REFERENCE TO RELATED APPLICATION

Figure 1:
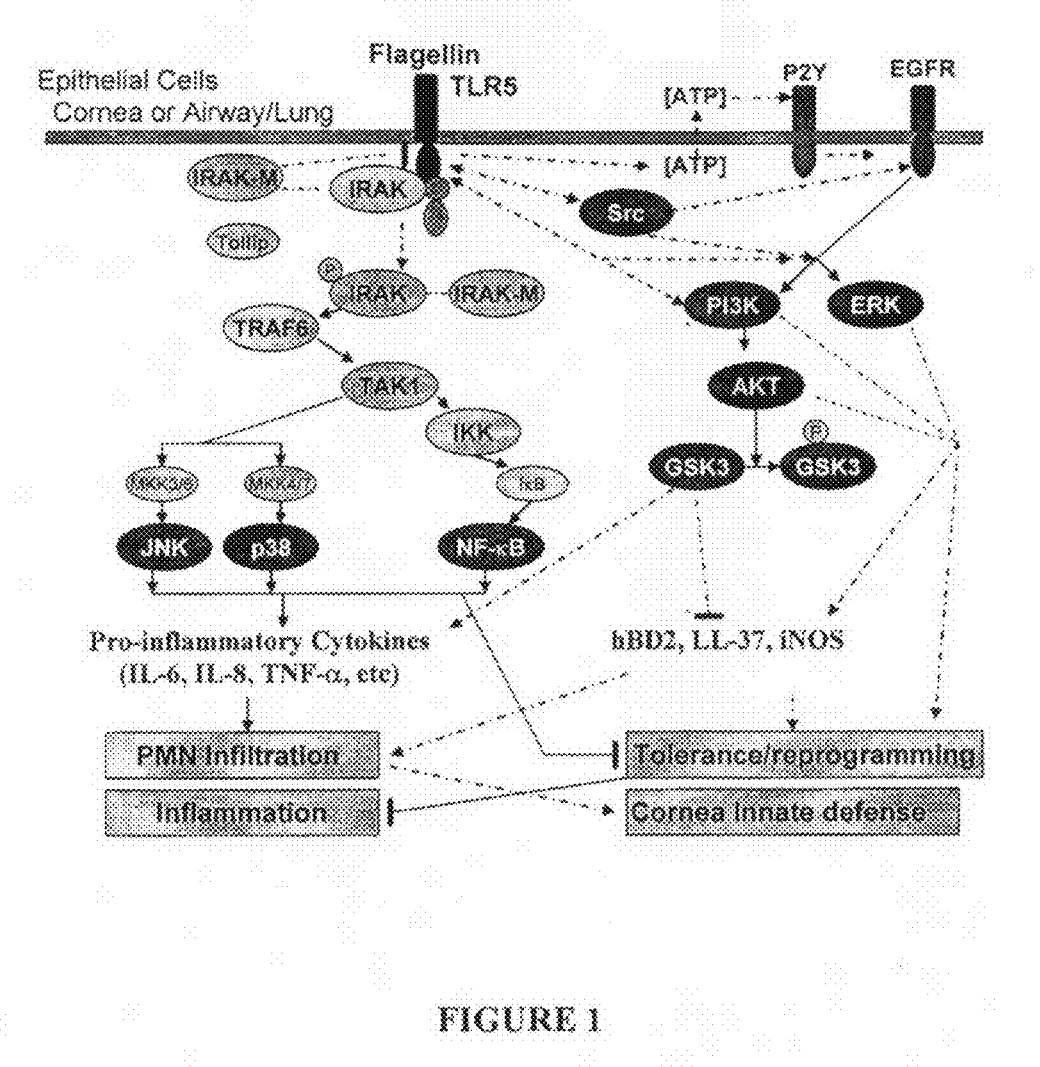

This application claims priority to provisional application Ser. No. 60/773,919, filed on Feb. 16, 2006, which is incorporated herein by reference in its entirety.

STATEMENT REGARDING FEDERALLY SPONSORED RESEARCH

This work was partially funded by National Institutes of Health/National Eye Institute Grants R01EY14080 and R01EY10869, and the United States government has, therefore, certain rights to the present invention.

TECHNICAL FIELD OF THE INVENTION

The invention relates to use of flagellin to treat and control keratitis. The invention also relates to the use of flagellin to induce innate protection and reduce inflammation associated with infection in other organs, including the lung.

BACKGROUND OF THE INVENTION

*Pseudomonas aeruginosa* keratitis is a sight-threatening corneal disease associated with trauma and contact-lens wearing. Although an antibiotic regimen can eliminate the infectious organisms, the host inflammation that occurs, if not suppressed, can cause corneal scarring that potentially leads to permanent vision loss in some patients.

The integrity of the cornea depends upon a tightly regulated host defense apparatus. Bacterial keratitis requires prompt diagnosis and treatment to prevent vision loss (Jeng, B. H., et al., Microbial keratitis *Br J Ophthalmol* 87:805-806). As such, it is recognized as a significant public health problem. Bacterial infection of the cornea generally occurs only when the corneal epithelial barrier function is compromised (Kurpakus-Wheater, et al., 2001 *Prog Histochem Cytochem* 36:185-259. McClellan, K. A. 1997 *Surv Ophthalmol* 42:233-246). There is a need in the art for materials and methods to treat keratitis.

*Pseudomonas aeruginosa* is implicated in other serious medical conditions. The bacterium is widespread in the environment and causes repeated infection in most Cystic Fibrosis (CF) patients. Initially, the infection can be addressed by aggressive treatment with antibiotics. However, *P. aeruginosa* infections often become permanent; it is estimated that more than eighty percent of adults with CF are chronically infected with *P. aeruginosa*. The chronic infection and inflammation associated with *P. aeruginosa* accelerate damage to the lungs, leading ultimately to respiratory failure and death. There have been many attempts to treat such patients with anti-inflammatory agents (Auerbach H S, et al., Lancet 1985:686-688; Sordelli D O, et al. Int. J. Immunopathol. Pharmacol. 1994; 7(2):109-117; Konstan M W, et al. N. Engl. J. Med. 1995; 332(13):848-854; Bisgaard H, et al. Amer. J. Respir. Crit. Care. Med. 1997:156(4); 1190-1196). However, there continues to be a need in the art for treatment and prevention of the chronic inflammatory conditions caused by bacterial infection in CF patients, as well as patients afflicted with other chronic infections and related inflammatory conditions of lung.

SUMMARY OF THE INVENTION

The invention provides methods for treating an eye disorder. The methods comprise a step of locally administering a flagellin polypeptide to the eye of a mammal to treat the disorder, by inducing tolerance to an infectious agent, particularly Gram-negative bacteria. In some embodiments, the methods comprise a step of locally administering a flagellin polypeptide to a cornea of a mammal to treat the disorder. A flagellin polypeptide may be administered topically to the cornea to treat the eye disorder.

The eye disorder may be associated with an inflammation of the eye. Examples of eye disorders associated with an inflammation include, but are not limited to, keratitis, bacterial conjunctivitis, fungal conjunctivitis, viral conjunctivitis, uveitis, keratic precipitates, macular edema, and inflammation response after intra-ocular lens implantation.

The invention provides compositions that may be employed for treating or preventing eye inflammation or infection, referred to as an eye disorder. The compositions comprise an ophthalmically acceptable carrier, a flagellin polypeptide in an amount effective to induce tolerance to a Gram-negative bacterial infection when the composition is administered to an eye, and optionally polyanionic component in an amount effective to provide lubrication to an eye when the composition is administered to an eye. In some embodiments, the composition is a solution. The polyanionic component may be an anionic cellulosic derivative (e.g., carboxy methyl celluloses).

The invention also provides flagellin polypeptides for administration to the airway and lung to prevent or alleviate inflammation related to bacterial infection, such as infection by *Pseudomonas aeruginosa*, particularly in patients suffering from cystic fibrosis. When pulmonary infection occurs in the setting of impaired innate and acquired immune responses, antimicrobial agents alone often cannot cure the host.

DETAILED DESCRIPTION OF THE DRAWINGS

FIG. 1 is a diagram showing TLR5 mediated epithelial tolerance in the cornea. When epithelial cells are exposed to *Pseudomonas aeruginosa*, TLR5 at the cell surface recognizes flagellin and activates several signaling pathways including NF-κB, p38 and JNK that lead to an inflammatory response. TLR5 also activates PI3K that negatively regulates the inflammatory response. After TLR activation, negative feedback mechanisms are also invoked, leading to down-regulation of the NF-xl3 pathway and augmentation of the PI3K pathway and resulting in tolerance/adaptation and greatly enhanced innate defense ability.

Figure 2:
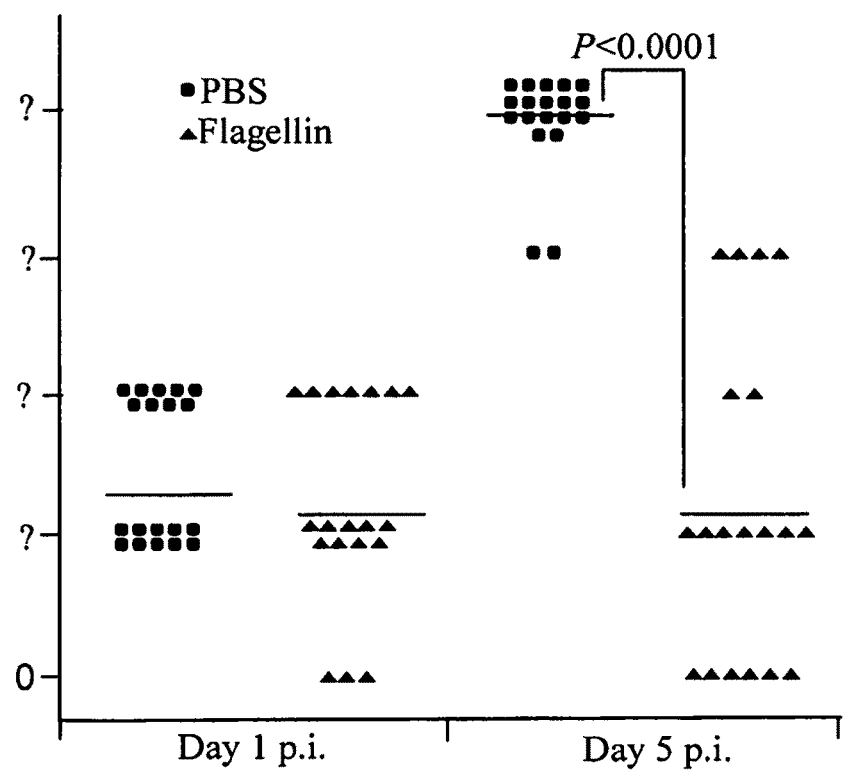

FIG. 2 shows the ocular disease clinical scores in flagellin-pretreated compared to PBS-injected mice at 1 and 5 days post infection with PA strain 19660. Flagellin pretreatment greatly improve the outcome of *Pseudomonas aeruginosa* keratitis in B6 mice.

Figure 3:
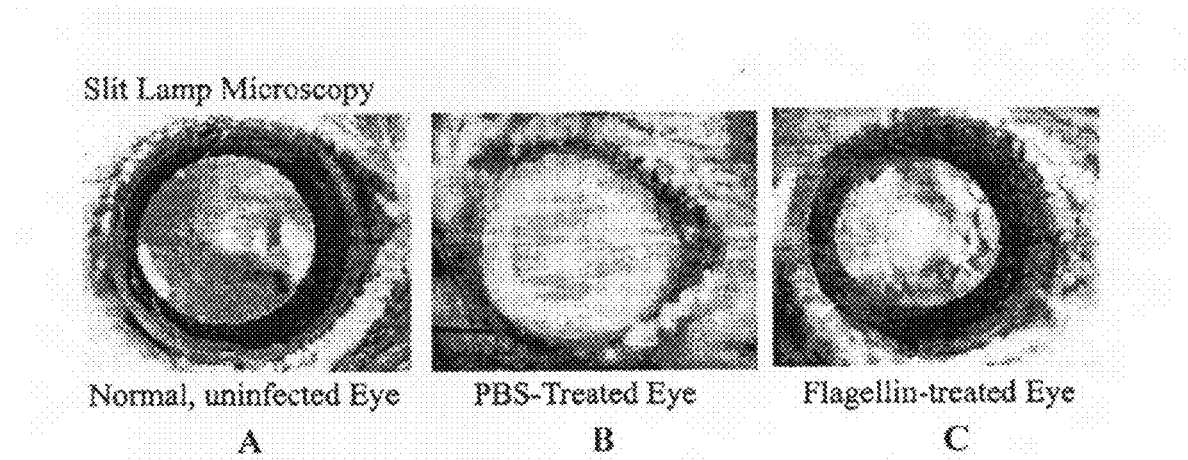

FIGS. 3A, B and C are slit lamp photographs at day 5 postinfection with PA strain 19660. FIG. 3A, normal eye. FIG. 3B shows that the cornea was perforated in the PBS-injected mice. FIG. 3C shows that slight opacity was observed in cornea pretreated with flagellin. The arrow in FIG. 3C shows PMN sediments.

Figure 4:
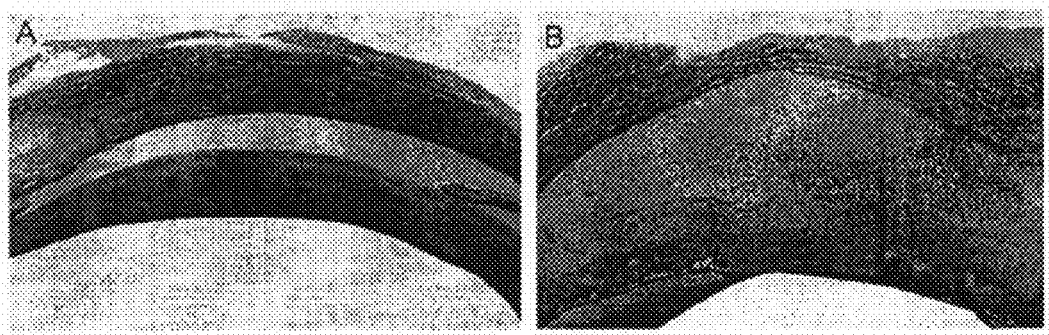

FIGS. 4A and B are cross-section photographs of the corneas shown in FIGS. 3B (4B) and C (4A) and show histopathological examination of *P. aeruginosa* strain 19660 infected cornea pretreated with (A) or without (B) flagellin. Flagellin pretreatment preserves the structural integrity of the cornea and prevents tissue destruction associated with *Pseudomonas aeruginosa* infection.

Figure 5:
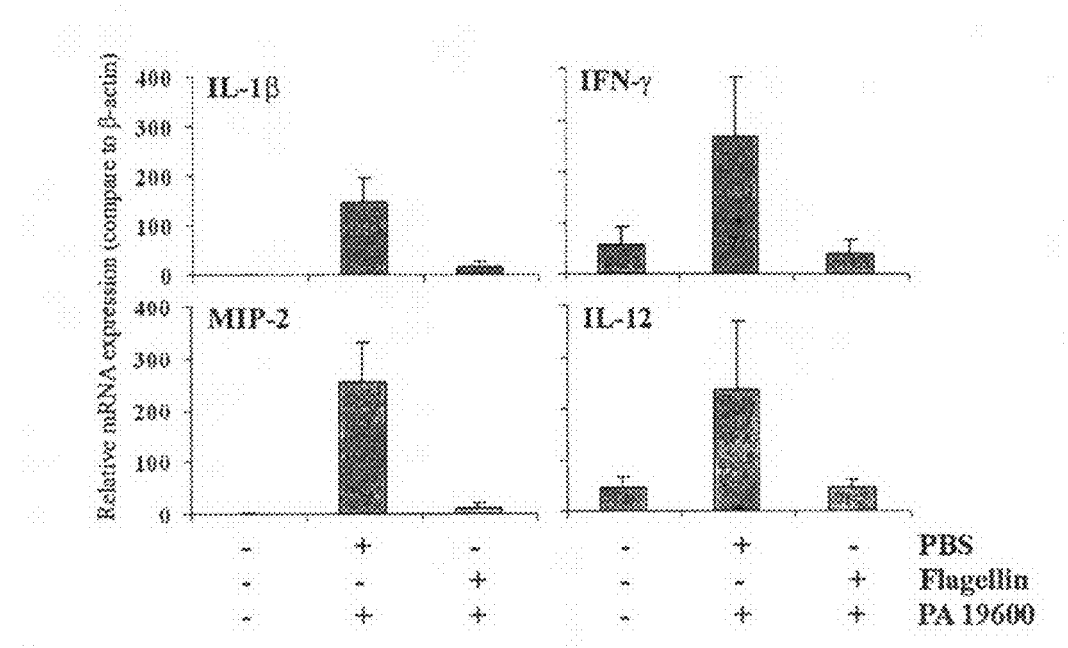

FIGS. 5A, B, C and D show mRNA expression of corneal IL-1β, MIP-2, IFN-γ, and IL-12 at 5 days p.i. with *P. aeruginosa* strain 19660. Corneas pretreated with flagellin showed significantly diminished expression of IL-1β and MIP2 (human IL-8 homolog) compared to corneas treated with PBS.

Figure 6:
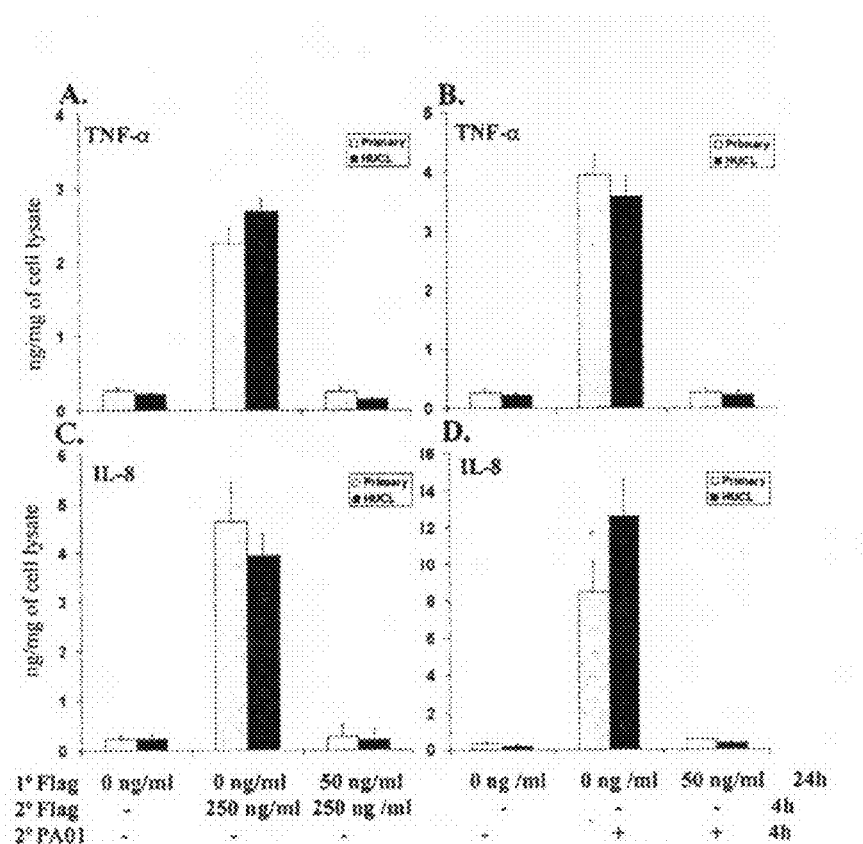

FIGS. 6A, B, C, and D show flagellin-induced tolerance to a second flagellin or PA01 challenge in the production of TNF-α and IL-8. Primary HCEC (passage 3, solid bars) or HUCL cells (gray bars) were cultured with or without 50 ng/ml flagellin for 24 h. After being washed twice with PBS, these cells were stimulated with 250 ng/ml flagellin (A and C) or live PAO1 (B and D) for 4 h. TNF-α (A and B) and IL-8 (C and D) secretion into culture supernatants was assayed by ELISA. Flagellin-induced tolerance dampens HCEC inflammatory response to flagellin and *P. aeruginosa* challenge in human corneal epithelial cells.

Figure 7:
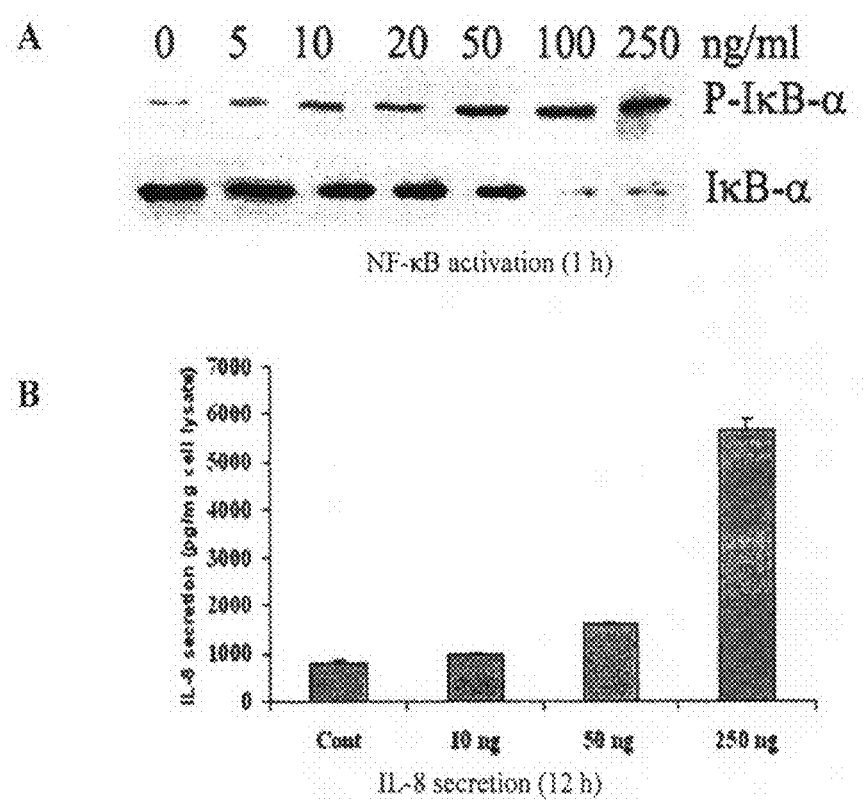

FIG. 7 shows flagellin dose dependent NF-κB activation and IL-8 production. HUCL cells were treated with various doses of fg for 1 h (A) or 12 h (B). (A) The cells were then lysed and subjected to Western blotting of phospho- (p-IκB-α) and total IκB-α (IκB-α). (B) The media were collected from cells for ELISA analysis to determine IL-8 secretion. Fg (50 ng/ml) induces NF-κB activation, but minimal inflammatory reaction (<2 fold increase in IL-8 production).

Figure 8:
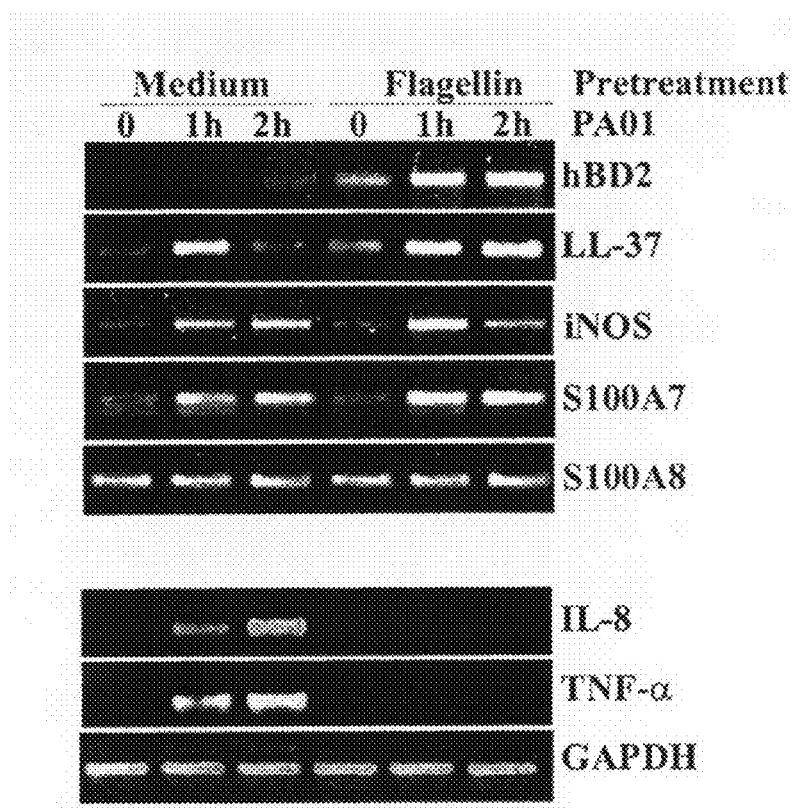

FIG. 8 shows the expression of specific mRNA. Corneal epithelial cells were pretreated with 50 ng/ml flagellin for 24 and then challenged with *P. aeruginosa*. At the indicated times (0, 1 hour, and 2 hour), cells were processed for semi-quantitative RT-PCR to assess mRNA expression of antimicrobial peptides (human beta-defensin 2, LL-37, iNOS-to produce NO—, and S100A7. Flagellin pretreatment either had no effects, or augmented the expression of antimicrobial genes while blocking *P. aeruginosa*-induced IL-8 and TNF-α expression in human corneal epithelial cells.

FIGS. 9A and B PMN infiltration and bacterial clearance in flagellin-pretreated corneas. Mice were treated with PBS or flagellin for 24 h, followed by ocular inoculation of $1 \times 10^6$ CFU of *P. aeruginosa* ATCC strain 19660 per cornea. At day 1 and day 5 postinfection, the corneas were excised and subjected the determination of MPO activity as the parameter for PMN recruitment (A) or plate bacterial counting (B). Flagellin pretreatment dose not affected PMN infiltration into cornea at the early stage of corneal infection but significantly decrease the number of bacteria in the infected corneas. At day 5 post-infection, both PMN infiltration and the number of bacteria are greatly reduced in the flagellin pretreated corneas, compared to the control, PBS treated corneas. Pretreatment of mice with flagellin enhances innate bacterial killing of the cornea, leading to the control of *P. aeruginosa* infection in B6 mice.

Figure 10:
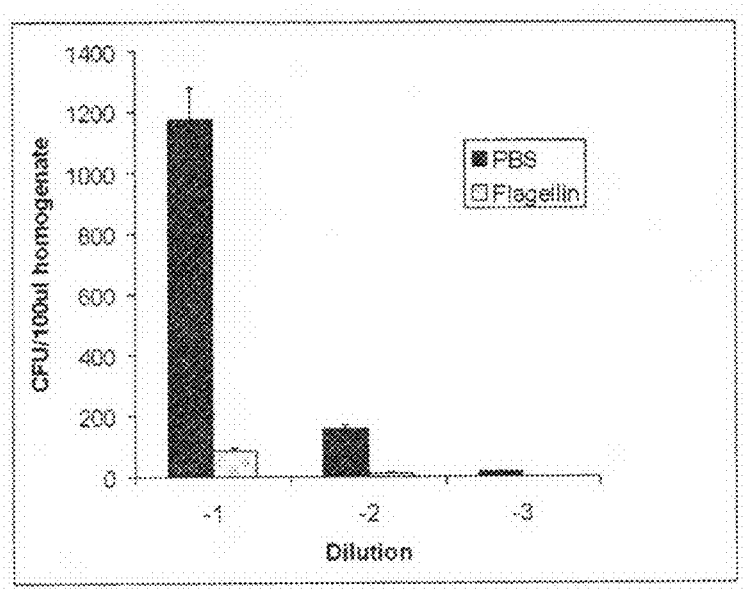

FIG. 10 is a bar graph showing bacterial clearance in the cornea treated with flagellin by subconjunctival injection. C57BL/6 mice were subconjunctivally injected with either PBS or flagellin (100 ng/eye). One day after the injection, the cornea was inoculated with *P. aeruginosa* ATCC strain 19660. At day 5 post-infection, the corneas were excised and subjected to plate bacterial counting. Administration of flagellin through subconjunctival injection only can enhance the bacterial clearance in the B6 mice.

Figure 11:
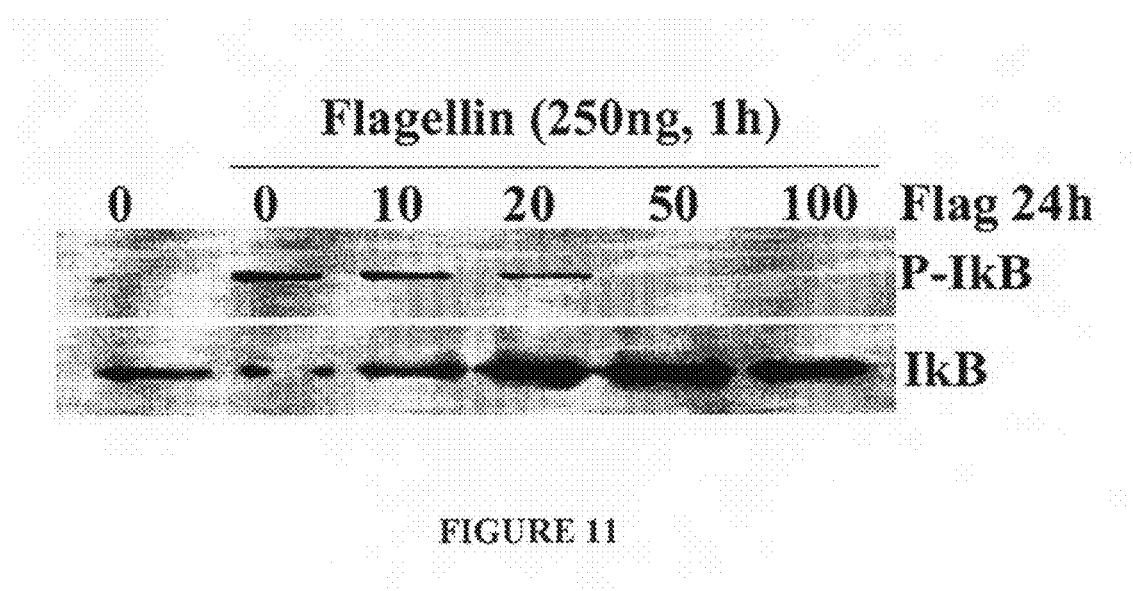

FIG. 11 shows tolerance induced by flagellin in human airway epithelial cells. Human airway epithelial cells (16HBE14o-) were pretreated with different concentrations of flagellin for 24 h and then challenged with 250 ng/ml flagellin. The activation of NF-κB was assessed with IκB phosphorylation and degradation. Pre-exposure of airway epithelial cells blocked NF-κB activation induced by further challenge of high dose flagellin in airway epithelial cells, indicating tolerance induced by low dosage flagellin in airway epithelial cells.

Figure 12:
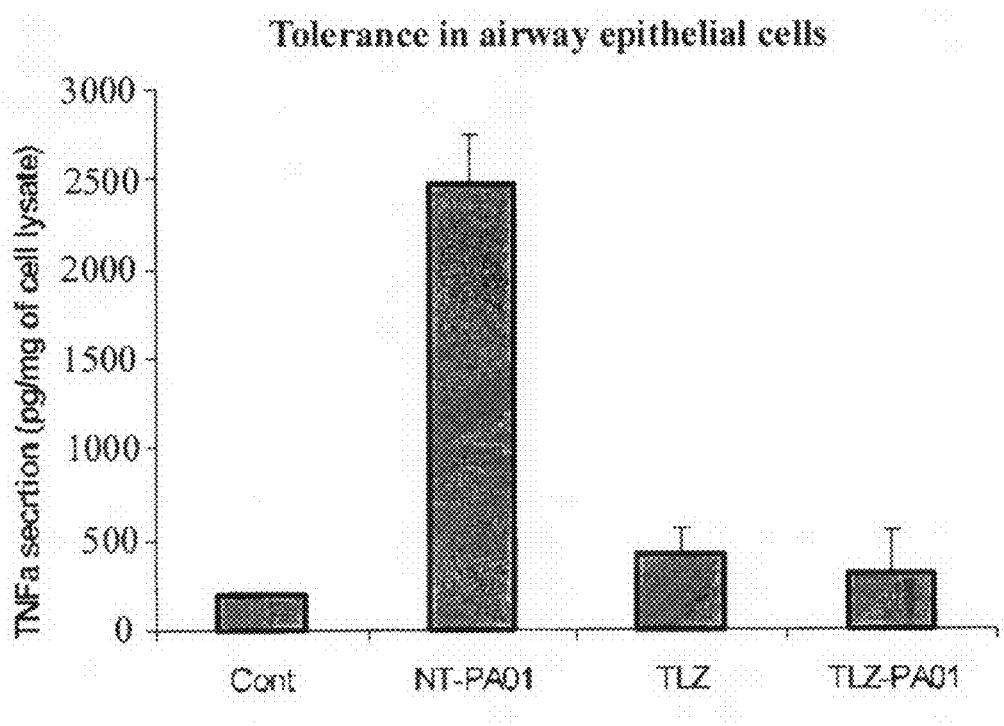

FIG. 12 shows flagellin-induced tolerance to live bacterial challenge in term of TNF-α production in human airway epithelial cells. Human airway epithelial cells (16HBE14o-) were pretreated with 50 ng/ml flagellin for 24 h and then challenged with live *P. aeruginosa*. The expression of proinflammatory cytokine TNF-α was measured. Pre-exposure of cells to flagellin blunted inflammatory response of airway epithelial cells to live bacterial challenge.

DETAILED DESCRIPTION

Previous studies by the inventors revealed that human corneal epithelial cells (HCECs) sense *Pseudomonas aeruginosa* (PA) via recognition of flagellin (fg) by Toll-like receptor-5 (TLR5) and respond to PA-challenge by producing pro-inflammatory chemokines and cytokines. To date, how the corneal inflammatory response is modulated after TLR stimulation is largely unresolved. The inventors have discovered that a prior exposure to low dose fg resulted in tolerance and adaptation in HCECs and in the cornea, as manifested by greatly decreased production of pro-inflammatory cytokines in vitro and significantly improved the outcome of PA infection in C57BL/6 (B6) mice. TLR-mediated epithelial adaptation or reprogramming therefore may be a key determinant of corneal inflammation, and the underlying mechanisms can be exploited as novel approaches for therapy.

HCECs detect Gram-negative bacteria such as PA via Toll-like receptor-5 recognition of flagellin and respond to PA challenge by producing pro-inflammatory cytokines and chemokines. Although this response is important for the host defense against invading pathogens, an inability to regulate inflammation is detrimental. To date, the underlying cellular mechanisms that modulate inflammatory response after TLR stimulation are largely unresolved. As disclosed herein, a prior exposure of HCECs to low dose fg results in PA tolerance in HCECs, as manifested by impaired NF-κB activation and greatly decreased production of pro-inflammatory cytokines in response to PA challenge. Phosphatidylinositol 3-kinase (PI3K) signaling is augmented during the course of tolerance development and TLR-mediated expression of inducible nitric oxide synthase, B-defensin-2, LL-37 and manganese superoxide dismutase (referred to as "protective genes") are either not affected or augmented by the tolerance phenotype.

Furthermore, the inventors show herein that fg administered prior to bacterial infection is able to prevent the expected corneal perforation and to significantly improve the outcome of PA infection in C57BL/6 mice. These data suggest that tolerance may be inducible in vivo in epithelial and/or other cells that serve to attenuate keratitis. Hence, although the mechanism is not essential to practicing the invention, fg-induced PA tolerance can be used as a model to delineate mechanisms that underlie TLR-mediated adaptation and reprogramming in the cornea.

The epithelium is capable of recognizing Gram-negative bacteria by TLR5-flagellin (fg) interaction, resulting in the production of pro-inflammatory cytokines and chemokines (Zhang, J., et al., 2005 *Curr Eye Res* 30:527-534; Zhang, J., et al., 2003 *Invest Ophthalmol Vis Sci* 44:4247-4254. Kumar, A., et al., 2004 *Invest Ophthalmol V is Sci* 45:3513-3522; Kumar, A., et al., 2006 *Immunology* 117:11-21; Li, H., et al., 2006 Immulogy 1117:167-176). Corneal inflammation is a two edged sword that requires careful regulation (Kurpakus- Wheater, 2001 *Prog Histochem Cytochem* 36:185-259). Following pro-inflammatory stimulation, negative feedback mechanisms should be invoked to induce the resolution of inflammation and to restore homeostasis, and as disclosed herein, exposure of HCECs to low doses of fg results in HCEC tolerance, as manifested by a muted cytokine burst in HCECs in response to PA challenge termed "PA tolerance," a term derived from "endotoxin tolerance" (West, M. A., et al., 2002 *Crit. Care Med* 30:S64-S73).

One finding of this invention is that while the initial low fg dose used to induce PA tolerance causes only minimal pro-inflammatory cytokine production, these fg-pretreated cells are tolerant not only to the subsequent high fg dose, but also to live PA challenge. Moreover, the present disclosure shows that TLR-mediated up-regulation of several genes with protective function including β-defensin, LL-37 and iNOS are unaffected or even augmented in tolerized HCECs. The produced β-defensin and LL-37 function as natural antibiotics and NO produced by iNOS also participate in bacterial killing whereas MN-SOD protects the host cells from damage caused by host inflammation and pathogenic factors. Hence, TLR5-mediated tolerance to bacteria may reflect a functional switch of HCECs rather than a general hyporesponsiveness to fg, and that the tolerance phenotype is the result of cell adaptation or reprogramming. Although the TLR signaling pathways leading to inflammatory response have been well documented (Yu, F., et al., 2006 *Invest Ophthalmol V is Sci* 47:1255-1263), the mechanisms and the consequences of TLR tolerance remain poorly understood.

TLR5, through recognition of fg, is a major sensor of Gram-negative bacteria and purified fg stimulates NF-κB activation and IL-6 and IL-8 production in HCECs in a TLR5-dependent manner (Zhang, J., et al., 2003 *Invest Ophthalmol V is Sci* 44:4247-4254). Fg is necessary and sufficient to trigger inflammatory responses caused by bacteria in tracheal columnar (Tseng, J., et al., 2005 *Am J Physiol Cell Physiol.*; Zhang, Z., et al., 2005 *Infect Immun* 73:7151-7160), human lung epithelial (Liaudet., et al 2003, *Shock* 19 131-137), and intestinal epithelial cells (Tallant, T., et al., 2004 *BMC Microbiol* 4:33. Ramos, H. C., et al., 2004 *Trends Microbiol* 12:509-517). Fg therefore is an important stimulus of key signaling pathways leading to an inflammatory response in epithelial cells such as corneal epithelial and airway/lung epithelial cells Fg-induced tolerance in HCECs represents an excellent model to study the underlying mechanisms. Based in part on this model, the invention provides new and improved therapies for treating or preventing bacterial keratitis as well as other diseases such as sepsis, cystic fibrosis, and inflammatory bowel disease. The invention also provides for use of flagellin in treating airway and pulmonary infection, particularly cases where tolerance curbs the inflammatory response, induces the expression of antimicrobial molecules and therefore increases bacterial clearance and reduces the destructive effect precipitated by overproduction of inflammatory cytokines. A model of how HCECs, via the action of TLR5, modulate the host response by acting either as a pro-inflammatory "sensor" or anti-inflammatory "dampener," is illustrated in FIG. 1.

Cystic fibrosis (CF) is the most common lethal inheritable disease affecting Caucasians. CF is caused by mutations in the gene encoding cystic fibrosis transmembrane conductance regulator (CFTR), resulting in multiorgan malfunctions. The lung complications in CF include chronic respiratory infections, which are the main cause of CF remaining an incurable lethal disease. The predominant CF pathogen is *Pseudomonas aeruginosa*: the lungs of >90% of all CF patients eventually become colonized with this bacterium.

A classical feature of *P. aeruginosa* strains infecting CF patients is that the motile, nonmucoid *P. aeruginosa* strains converts to a mucoid, exopolysaccharide alginate-overproducing form in a process referred to as the conversion to mucoidy. The conversion to mucoidy is concomitant with the establishment of chronic bacterial colonization. Infections with mucoid *P. aeruginosa* are associated with heightened inflammation, tissue destruction, and pulmonary function decline. Hence, *P. aeruginosa* employs a strategy to promote survival in the cystic fibrosis lung.

*P. aeruginosa* can shut down the expression of flagellin, leading to the loss of flagella and motility. Flagellin is a potent stimulator of the host immune response via Toll-like receptor 5. The addition of flagellin to human airway epithelial cells induces the transcription of many genes encoding pro-inflammatory mediators such as IL-8. *P. aeruginosa* quickly down-regulates transcription and expression of flagellin when exposed to either normal or cystic fibrosis sputum. This response is thought to help *P. aeruginosa* evade detection by the immune system, particularly TLR5. Since the conversion to mucoidy confers a selective advantage in the pulmonary environment for bacteria, administration of flagellin may create a pulmonary environment in which host immune system treat the mucoid form as normal, nonmucoid phenotype, as such to enhancing host defense response, resulting in ride of colonized bacteria. This use of flagellin is encompassed by the present disclosure.

Despite advances of modern medicine, bacterial sepsis remains one of the major threats to human health worldwide. In the US alone, it affects approximately 750,000 Americans per year, with an associated mortality rate greater than twenty eight percent. Mortality largely is the result of excessive inflammation; reducing the inflammation by flagellin exposure as described herein, in combination with antibiotic treatment, may reduce the septic shock and accelerate recovery after sepsis.

Asthma is a highly prevalent and serious health problem for which no therapy currently offers the hope of a cure. Decreased exposure to infection or environmental pathogenic factors released from bacteria in early childhood has been linked to the increased incidence of asthma in industrialized countries, according to the hygiene hypothesis. As such, exposure of a low dosage of flagellin may be considered an effective way to prevent asthma development, and a novel therapeutic tool for the treatment of asthma.

The invention also relates to therapeutic application of flagellin to control infection in the cornea. Although an antibiotic regimen can eliminate the infectious organisms, the host inflammation that occurs, if not suppressed, can cause corneal scarring that potentially leads to permanent vision loss in some patients (Kurpakus-Wheater, et al., 2001 Prog Histochem Cytochem 36:185-259).

At present, only corticosteroids are available in ophthalmic solutions to suppress the ongoing inflammatory response after bacterial corneal infection although their effect (beneficial or detrimental) in reducing host-mediated tissue damage has not been proven conclusively in bacterial keratitis (Wilhelmus, K. R., et al., 2002 *Ophthalmology* 109:835-842). Therefore, the controversial role of corticosteroids and emerging resistance of PA to antibiotics warrant development of new adjunctive therapeutic modalities.

Fg-pretreatment attenuates pathogenesis of PA-keratitis in C57BL/6 (B6) mouse model, so the underlying mechanisms of TLR-tolerance may be exploited for dampening inflammation and even controlling infection. As shown in the Examples herein, infiltration and a much improved clinical score from day 3 to day 5 were observed in fg-pretreated corneas of PA-infected B6 mice. Without being hound by a particular mechanism, the invention postulates that fg-pretreatment induces tolerance and reprogramming in cornea, likely first in the epithelium, but may include infiltrated cells. This tolerance dampens inflammation but not PMN infiltration that is important for bacterial clearance. The additional protective force may come from enhanced epithelial innate killing ability related to the generation of h-β-defensin, LL-37 and NO (products of iNOS) as well as accelerated wound healing in TLR5 tolerized mice.

The dampening of inflammation may also occur at the level of the infiltrated PMNs, resulting from a selective reprogramming of PMN function induced by fg-pretreatment or by tolerized epithelial cells. This should limit PMN responses in vivo and prevent excessive cell activation, which could culminate in tissue damage (Parker, L. C., et al., 2005 *J Leukoc Biol* 78:1301-1305). Animal models allow the elucidation of the effects of tolerance induction on PMN infiltration, corneal inflammation and resolution, vascularization, and epithelial wound healing and functional recovery. The use of fg and other reagents shown herein in vitro to enhance tolerance (such as GSK3 inhibitors) as an adjuvant therapy may dampen inflammation while bacteria are killed by antibiotic treatment in vivo. A well-characterized and -accepted animal model of PA-keratitis is available and used in the Examples below (Hazlett, L. D., et al., 2000 *Invest Ophthalmol V is Sci* 41:805-810; Huang, X., et al., 2005 *Invest Ophthalmol V is Sci* 46:4209-4216; Thakur, A., et al., 2004 *Invest Ophthamol V is Sci* 45:3177-3184).

Epithelial lining plays a key role in innate defense including the recognition and response to bacterial infection. Upon recognition of pattern associated molecular patterns through Toll-like receptors, epithelia initiate inflammatory response by secretion of proinflammatory cytokines that induce infiltration that is necessary for clearance of bacterial infection and yet may cause tissue destruction such as that observed in septic shock, airway inflammation, ocular keratitis, and inflammation bowel diseases.

Pre-exposure of epithelia to low concentration of bacterial flagellin induces "tolerance" as manifested by decreased proinflammatory cytokine production and reduced responsiveness to bacterial infection. In vivo testing provided similar results using the mouse model of keratitis. Therefore, flagellin at a dosage that causes no inflammatory response, but induces tolerance, may be used as an anti-inflammatory therapy for treating sepsis, pulmonary infection in patients with cystic fibrosis, acute exacerbations of chronic obstructive pulmonary disease, keratitis, Crohn's disease and inflammatory bowel disease. As demonstrated herein, activation of TLRs also leads to restored cell homeostasis following pro-inflammatory stimulation, so flagellin stimulation of TLR5 may also be used to promote healing after inflammatory injury.

Instead of treating inflammation as traditionally understood, the methods herein use a Gram-negative bacterial component to stimulate epithelial cells to a level that will not cause inflammation, but lead to tolerance/reprogramming that alters the state of immunity in the body and blunts inflammation caused by Gram-negative bacterial infection. The invention discloses for the first time that flagellin induced tolerance, and this unique Toll-like receptor ligand (the only known TLR ligand that is a protein) can be exploited to reduce the tissue damages caused by inflammation associated with infection and other inflammation diseases.

Negative feedback mechanisms are key in restoring homeostasis after inflammation/infection. The present approach induces adaptations after initial inflammatory response. By manipulating cell sensitivity to bacterial infection or other inflammation-inducing conditions, the treatment may blunt inflammation in vivo without rendering the host susceptible to tissue destruction or systemic dissemination of infection and/or inflammation.

Unlike lipopolysaccharide, which has been proposed to induce tolerance to treat septic shock, flagellin, although a potent inflammatory stimulus, is not expected to be cytotoxic. The present disclosure teaches concentrations wherein cells can be activated, as assessed by NF-κB activation, but not produce proinflammatory cytokines as assessed by ELISA. This concentration is sufficient to induce cell tolerance.

Targeting the effector of PI3K/AKT pathway, GSK3-β, has been shown by the inventors to potently suppress the pro-inflammatory response in HCECs and in mice challenged with LPS that protects the mice from endotoxin shock (Martin, M., et al., 2005 *Nat Immunol* 6:777-784). The results from the Examples herein reveal the role of PI3K/AKT/GSK3-β in tolerance induction of HCECs, and this not only provides evidence for the role of PI3K in in vivo tolerance induction, but also provides experimental basis for the use of GSK3 inhibitors as an effective therapeutic agent against microbial keratitis.

Using approaches discussed in the Examples, the invention provides that targeting GSK3 with inhibitors, alone or with fg-pretreatment, modulates the inflammatory response of the corneas in response to PA infection. Although the mechanism is not binding, if administration of GSK3-β inhibitor(s), alone or with flagellin, prior to or during bacterial infection attenuates the production of pro-inflammatory cytokine and improves the outcome of the disease, this supports the conclusion that the PI3K/AKT/GSK3-β pathway plays a key role in attenuating microbial keratitis by inhibiting corneal inflammatory response in vivo. These findings will be clinically relevance since the small molecular inhibitors such as SB216763 or pharmaceutical-grade inhibitors (Woodgett, J. R., et ak., 2005 *Nat Immunol* 6:751-752) might be used as anti-inflammatory agents to stop disease progression during antibiotic sterilization of the cornea.

Other Examples herein revealed that while control corneas were perforated at day 5 post-infection with PA, the fg-pre-treated corneas up to that time were scored at average ~+1 (slight opacity, fully covering the anterior segment). This is of great significance as tolerance provides a large window of time for the use of antibiotics to eliminate the bacteria before irreversible damage occurs, thus preserving the cornea and vision after PA infection. Blunting the inflammation and increase innate defense ability by fg-treatment during sterilization of the cornea by antibiotics is clinically applicable.

By the time a patient visits a doctor for treatment of an eye infection, infection has already occurred and disease already progressed to certain level. In an animal model of keratitis, a time point is expected at which the treatment of antibiotics is unable to prevent corneal perforation since, while the invading bacteria might be eliminated, the inflammation will continue, leading to tissue damage. Including fg and/or GSK3 inhibitor as an anti-inflammatory agent may significantly extend the time required for initiation of antibiotic regimen before the disease becomes irreversible. This is clinically significant as it will greatly extend the window of time for effective antibiotic regimen in treating the patients. Although it might be too late to blunt the epithelial inflammatory response hours after infection occurs, fg or GSK3 inhibitor treatment is expected to exert effects on the infiltrated PMN and induce these infiltrated cells to become "tolerant" to PA, or at least attenuate the inflammatory cytokine burst of the PMN without excessively compromising their bacterial killing function.

Furthermore, when the invaded bacteria are eliminated by antibiotics, the presence of fg and/or GSK3 inhibitors may exert effects on the epithelial cells to enhance inflammatory dampening mechanisms and to promote epithelial wound healing, leading to functional recovery of the cornea. Much improved outcome of the disease is expected. In one Example discussed herein (?), the cornea becomes clear and disease free in mice treated with antibiotic and fg (or GSK3 inhibitor), providing a better prognosis than antibiotics alone, leading to the clinical use of fg as an adjunctive therapy to treat microbial keratitis.

A "flagellin polypeptide" as used herein may be any polypeptide that binds a naturally occurring TLR5 and triggers at least one of the biological functions of the TLR5 in antigen-presenting cells upon such binding. Thus, a flagellin may be a polypeptide comprising any of the naturally occurring bacterial flagellin proteins. A flagellin may also be a polypeptide that is substantially identical with any of the naturally occurring bacterial flagellin proteins at the amino acid sequence level, wherein the polypeptide is capable of binding a naturally occurring TLR5. Furthermore, a flagellin may be a polypeptide that is substantially identical with the 170 residues from the N terminus and 90 residues from the C terminus of any of the naturally occurring bacterial flagellin proteins at the amino acid sequence level, wherein the polypeptide is capable of binding a naturally occurring TLR5. Any flagellin useful in this invention may be a fusion protein that comprises an unrelated peptide or protein, such as an antigen or the Fc portion of an immunoglobulin. The flagellin used herein may also comprise a modification, such as glycosylation or phosphorylation.

As used in the Examples herein, LPS-free flagellin was isolated and purified prior to use. Other flagellin polypeptides that can be assayed for biological activity within the scope of the claims are described in U.S. Patent Publication No. 20050147627.

Pharmaceutical Use

Treatment dosages should be initially titrated in development to optimize safety and efficacy. Typically, dosages used in vitro may provide useful guidance in the amounts useful for in situ administration of these reagents. Animal testing of effective doses for treatment of particular disorders is known in the art to provide further predictive indication of human dosage. Various considerations are described, e.g., in Gilman, et al. (eds.) Goodman and Gilman's: The Pharmacological Bases of Therapeutics, latest Ed., Pergamon Press; and Remington's Pharmaceutical Sciences, latest ed., Mack Publishing Co., Easton, Pa. Methods for administration are discussed therein and below, e.g., for direct application to the lung. Pharmaceutically acceptable carriers will include water, saline, buffers, and other compounds described, e.g., in the Merck Index, Merck & Co., Rahway, N.J.

Dosage ranges would ordinarily be expected to deliver amounts that result in mucosal surface liquid concentrations of 500 nM concentrations, typically less than about 1 μM concentrations, preferably about 400 μM, preferably not less than about 100 nM. Slow release formulations, or a slow release apparatus may be utilized for continuous or long term administration. See, e.g., Langer (1990) Science 249:1527-1533. Dose evaluation may depend, e.g., on patient weight, age, condition, and other relevant variables. Exemplary dose ranges should account for total area surface liquid (ASL) and estimated sputum volumes. It is expected that normal amounts would be about 400 nM. A range of 100 fold lower or higher should be tested, as the balance of excess activity vs. tolerable damage from excess may depend upon patient condition. Estimating ASL of about 10 ml and sputum volume is estimated to another 10 ml, then a dose of about 2 μg (in 1 ml) is delivered in the volume of deposited aerosol.

Therapeutic formulations may be administered in many conventional dosage formulations. While it is possible for the active ingredient, flagellin polypeptide, to be administered alone, it is preferable to present it as a pharmaceutical formulation. Formulations typically comprise at least one active ingredient together with one or more acceptable carriers thereof. Each carrier should be both pharmaceutically and physiologically acceptable in the sense of being compatible with the other ingredients and not injurious to the patient. Formulations include those suitable for lung administration. The formulations may conveniently be presented in unit dosage form and may be prepared by many methods well known in the art of pharmacy. See, e.g., Gilman, et al. (eds. 1990) Goodman and Gilman's: The Pharmacological Bases of Therapeutics 8th Ed., Pergamon Press; and Remington's Pharmaceutical Sciences, 17th ed. (1990), Mack Publishing Co., Easton, Pa.; Avis, et al. (eds. 1993) Pharmaceutical Dosage Forms: Parenteral Medications Dekker, New York; Lieberman, et al. (eds. 1990) Pharmaceutical Dosage Forms Tablets Dekker, New York; and Lieberman, et al. (eds. 1990) Pharmaceutical Dosage Forms Disperse Systems Dekker, New York. The flagellin polypeptide of this invention may be combined with or used in association with other agents, e.g., known cystic fibrosis therapies, or suitable antibiotics for treating infections of the eye.

Various combinations of therapeutics may be used, e.g., with antibiotics, antifungal agents, antiviral agents, with various peroxidases, with sulfhydryl compounds, with $H_2O_2$, or other therapeutics or procedures used in the treatment of CF or other lung infections. Such procedures include airway clearance techniques (ACTs) and physiotherapy, e.g., breathing exercises, postural drainage, chest percussion, vibration, assisted coughing, and forced expiratory techniques. Other lung conditions will include those where infections may be problematic, e.g., tuberculosis, asthmatic conditions, artificially ventilated patients, HIV or other immunosuppressed individuals. As described above, there are various treatments for cystic fibrosis, which may be combined with the treatment described herein. Administration may be simultaneous or sequential, e.g., with the various other therapeutics, or with the DNAse (Pulmozyme®) or TOB™.

The invention also provides a method of locally treating or preventing a pulmonary condition in a patient in need therefore, wherein the pulmonary condition is selected from the group consisting of asthma, chronic obstructive pulmonary disease, and cystic fibrosis, the method comprising administering to the patient an aerosolized composition comprising flagellin. The aerosolized composition may further comprise at least one additional TLR ligand or TLR agonist. One such ligand is Pam3Cys (synthetic lipopeptide (S)-(2,3-bis(palmitoyloxy)-(2RS)-propyl)-N-palmitoyl-(R)-Cys-(S)-Ser(S)-$Lys_4$-OH, trihydrochloride), which is a synthetic ligand for TLR2 that recognizes Gram positive bacterial and fungus. Pam3Cys is discussed in Siedlar, M. et al., *The Journal of Immunology,* 173: 2736-2745 (2004). Another such ligand is CpG DNA for TLR9. This ligand has been used in clinical trials to prevent asthma, and recognizes bacterial and viral DNA. Yu, D. et al., (Nucleic Acids Research 30:1613-1619, 2002) discuss preparation and uses of CpG DNA.

The compositions of the invention are suitable for administration intravenously, orally, buccal, intraperitoneally, into the joint space, rectally, to the surface of the skin, transdermal (slow release preparation), subcutaneously, intramuscularly, intranasally, to the eyes as eye drops, and in contact solution, by intravitreal (i.e. into the eye) injection, or by aerosol (e.g. topically to the lungs) at a concentration ranging from 0.1 to 20 µg/ml. A suitable concentration is 0.5 µg/ml to 10 µg/ml.

Methods for administering pharmaceutical compositions to the lung are disclosed, for example, in U.S. Pat. Nos. 6,702,998 and 7,141,236. Methods for administering pharmaceutical compositions to the eye are disclosed, for example, in U.S. Pat. Nos. 6,569,443 and 6,315,996.

An animal model for pulmonary administration of flagellin to the lungs is described in Deng, J. C., et al. 2004, *J Immunol* 173:5148-5155; and Ballinger, M. N., et al., 2006. *Am J Respir Cell Mol Biol* 34:766-774. Flagellin polypeptides disclosed herein are tested at various doses for their ability to induce tolerance to Gram-negative bacteria in the lungs, and to reduce the inflammatory reactions to infection and to increase bacterial clearance in the airways and lungs.

The following examples are intended to illustrate but are not to be construed as limiting of the specification and claims in any way.

EXAMPLES

Example 1

Flagellin as Therapeutic Reagent to Induce Tolerance, to Dampen Inflammation, and to Control Infection An animal model of *Pseudomonas keratitis* with similar pathogenesis to human *Pseudomonas keratitis* was used in this Example. Eight-week-old female C57BL/6 (B6) mice were used in the following experiments. In each experiment, the left cornea of each anesthetized mouse was scarified with three parallel 1 mm incisions using a sterile $25^{5/8}$ gauge needle under a stereoscopic microscope. Scarified corneas were challenged topically with $1.0 \times 10^6$ CFU/µL of *P. aeruginosa* ATCC strain 19660 (cytotoxic strain) in a 5 µl dose. Eyes were examined macroscopically at daily day postinfection (p.i.) to monitor the course of disease visually. The cornea of the infected mice perforated within 5 to 7 days.

Lipopolysaccharide-removed flagellin purified from *P. aeruginosa* by the inventors was administrated subconjunctivally at a dosage of 100 ng/eye 24 h prior to bacterial infection. To ensure tolerance was induced in the mice, the mice were injected intraperitoneally (i.p.) with 125 ng fg/per mice. The next day, mice were challenged with *Pseudomonas aeruginosa* strain 19660. The corneal disease response was graded at 1, 3, and 5 days post infection (p.i.) using the following, previously described scale (Hazlett, L. D., et al., 2000 *Invest Ophthalmol V is Sci* 41:805-810): 0, clear or slight opacity, partially or fully covering the pupil; +1, slight opacity, fully covering the anterior segment; +2, dense opacity, partially or fully covering the pupil; +3, dense opacity, covering the entire anterior segment; +4, corneal perforation or phthisis.

The results are shown in FIG. 2. In 4 separate experiments (five or four mice per group, respectively), in the control, PBS injected mice, the disease progressed uniformly; at 24 hours, mice exhibited a +1 clinical score, which progressed to a +3 disease grade by day 3 p.i., and by day 5, all the infected corneas had perforated (+4); therefore, the experiments were terminated at day 5. From day 1 to day 5, the fg-pretreated mice exhibited less severe disease, but more variation in the disease grades as compared to the control mice. The average score for the fg-pretreated mice did not change much from day 1 to day 5 and was significantly lower at 3 (P=0.0002) and 5 days p.i. (P=0.0001). Thus, the fg-pretreatment prevents perforation and significantly improved the outcome after corneal infection using PA.

FIGS. 3A and B shows slit lamp photographs of ocular disease response in B6 mice pretreated with fg or PBS. Perforation and vascularization are evident in the control PBS injected eye (B), whereas the eye of fg-pretreated mice (A) shows only slight opacity (0/+1) with sediments of PMN laterally (Arrow). There was little or no vascularization in fg-pretreated corneas. Cross-section photographs are shown in FIGS. 4A and B, and show histopathological examination of *P. aeruginosa* strain 19660 infected cornea pretreated with (A) or without (B) flagellin.

Manipulation of TLR signaling has been attempted before to suppress keratitis in B6 mouse model (Huang, X., et al., 2005 *Invest Ophthalmol V is Sci* 46:4209-4216). In that study, subconjunctival injection of TLR9 siRNA, but not control, reduced the expression of TLR9 in epithelial cells and infiltrated PMN. Silencing TLR9 signaling was found not only to reduce inflammation but also to decrease bacterial killing in the cornea. At day 5, while most fg-pretreated eyes are scored +1 according to this Example, the TLR9 siRNA-treated eyes of the Huang study had progressed to a +3 disease grade, with some perforated. There was also sign of vascularization in TLR9 siRNA-treated eyes.

Because the present results differ from those reported by Huang, fg-pretreatment appears to represent a different mechanism from TLR silencing; it not only significantly reduced inflammation but also enhanced bacterial killing and controlled the progress of infection. It is likely that flagellin-pretreatment induces tolerance in the cornea, resulting in muted pro-inflammatory cytokine burst, enhanced production of antimicrobial and protective molecules, but minimally affecting PMN infiltration that contributes to bacterial clearance, as shown in TLR2 agonist-pretreated (Feterowski, C., et al., 2005 *Int Immunol* 17:1035-1046).

Comparison of the histology is shown in Table 1:

TABLE 1

| Pathology | Control | Flagellin pretreated cornea |
|---|---|---|
| Corneal edema | Yes | No |
| Epithelium | Totally lost | Largely preserved |
| Central stroma | Large Part Lost | Intact |
| Stromal infiltration | Heavy | Few infiltrating cells |
| Anterior chamber | Heavier cellular infiltrate | No visible infiltration |
| Lens and iris | Destroyed | No sign of pathology |

FIGS. 5A and B shows mRNA expression of corneal IL-1β and MIP-2 at 5 days p.i. with *P. aeruginosa* strain 19660. Corneas pretreated with flagellin showed significantly diminished expression of IL-1β and MIP2 (human IL-8 homolog) compared to corneas treated with placebo (PBS). Greatly reduced expression of representative proinflammatory cytokines IL-1β and MIP-2 would indicate that flagellin treatment can dampen inflammatory response in the cornea, and might be underlying reason for the great decreased pathology seen in FIGS. 3 and 4.

Figure 9:
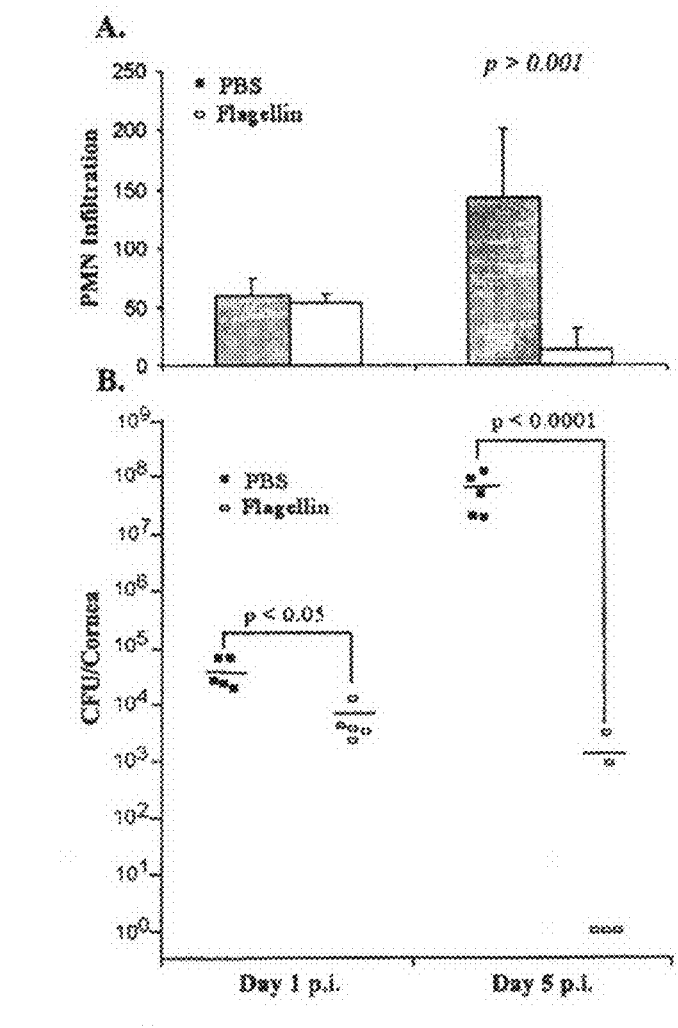

As shown in FIG. 9, C57BL/6 mice were subconjunctivally injected (100 ng/eye) with either PBS or flagellin. One day after the injection, the cornea was inoculated with *P. aeruginosa* ATCC strain 19660. At the indicated times after infection, the corneas were excised and subjected to plate bacterial counting. Administration of flagellin through subsubconjunctival injection greatly enhanced the bacterial clearance in the B6 mice.

Tolerance and reprogramming can also be induced in airway epithelial cells, and similar protection mechanisms are expected in vivo. Flagellin can be administrated in the airway and into the lungs by aerosolized flagellin. An animal model that can be applied to pulmonary administration of flagellin to the lungs is described in Deng, J. C., et al. 2004, *J Immunol* 173:5148-5155; and Ballinger, M. N., et al., 2006. *Am J Respir Cell Mol Biol* 34:766-774. Tolerance induction by flagellin in airway epithelial cells is shown in FIGS. 11 and 12.

As shown in FIG. 10, normal human airway epithelial cells were pretreated with different concentration of flagellin for 24 h and then challenged with 250 ng/ml flagellin. The activation of NF-κB was assessed with IκB phosphorylation and degradation. Pre-exposure of airway epithelial cells blocked NF-κB activation induced by further challenge of high dose flagellin in airway epithelial cells, indicating tolerance induced by low dosage flagellin in airway epithelial cells.

FIG. 11 shows that normal human airway epithelial cells were pretreated with (TLZ) or without (NT) 50 ng/ml flagellin for 24 h and then challenged with live *Pseudomonas aeruginosa* (PAO1). The expression of proinflammatory cytokine TNF-α were measured. As in human corneal epithelial cells, pre-exposure of cells to flagellin blunted inflammatory response of airway epithelial cells to live bacterial challenge, suggesting the same tolerance and protection may be induced in the respiratory system.

FIG. 12 shows flagellin-induced tolerance to live bacterial challenge in term of TNF-α production in human airway epithelial cells. Human airway epithelial cells (16HBE14o-) were pretreated with 50 ng/ml flagellin for 24 h and then challenged with live *P. aeruginosa*. The expression of proinflammatory cytokine TNF-α was measured. Pre-exposure of cells to flagellin blunted inflammatory response of airway epithelial cells to live bacterial challenge.

Example 2

Activation of HCECs by Flagellin-TLR5

TLR5 recognized *Pseudomonas aeruginosa* flagellin and triggered the expression and/or release of proinflammatory cytokines in human corneal epithelial cells (HCECs). In the present Example, assays were performed to determine whether activation of HCECs by flagellin-TLR5 results in tolerance as manifested by decreased cytokine production and hyporesponsiveness to subsequent *P. aeruginosa* infection.

HUCL, a telomerase-immortalized HCEC line, and primary culture of HCECs, were pretreated with low dosages 50 ng/ml of *P. aeruginosa* (PAO1) flagellin for a period of 12 to 24 h to induce tolerance. The flagellin-tolerized HCECs were then challenged either with higher dose of flagellin (250 ng/ml) or live *P. aeruginosa* at MOI of 50-100. The activation of NF-κB and MAPKs (p38, JNK, ERK) was assessed by Western blotting using phosphor-specific antibodies. RT-PCR was used to detect the changes in mRNA levels of negative-regulators of TLR-signaling pathways such as Tollip, SIGIRR, IRAK-M, IRAK1, and IRAK2. Secretion of pro-inflammatory cytokine/chemokines IL-6, IL-8, and TNF-α in the culture media was assessed using ELISA.

Prolonged incubation (12 to 24 h) of HUCL cells and primary HCECs with flagellin (as low as 10 ng/ml) induced a state of hyporesponsiveness (tolerance) characterized by impaired activation of TLR-down streaming signaling pathways such as NF-κB and MAPKs (p38, JNK, ERK) and reduced cytokine (IL-6 and IL-8) production upon subsequent second challenge with higher (250 ng/ml) doses of flagellin. Furthermore, priming of HCECs with flagellin greatly reduced the inflammatory response of HCECs, with diminished accumulation of cytokine/chemokines (IL-6, -8 and TNF-α) in their culture media upon live *P. aeruginosa* infection. Pre-treatment with flagellin did not alter the total protein levels of TLR5 and adaptor molecule MyD88.

In summary, exposure of HCECs to flagellin resulted in HCEC "tolerance", as manifest by greatly decreased cytokine production and hypo-responsiveness to PA challenge.

Example 3

Flagellin and Pam$_3$ Induced TLR Self-Tolerance but not Cross-Tolerance in HCECs This Example relates to the goal of exploiting the mechanism of tolerance as a novel approach for anti-inflammatory therapy. To be useful, TLR agonists used should be sufficient to induce tolerance or adaptation and yet not high enough to cause a robust inflammatory response in cells. To that end, 1 µg/ml Pam3 (a synthetic lipopeptide) was used (10 µg/ml was routinely used in the literature (Kumar, A., et al. 2005. Microbes Infect. 8:380-389), and 50 ng/ml PA fg (250 ng/ml was determine to give maximal stimulation; Zhang, J., et al. 2003. *Invest Ophthalmol Vis Sci* 44:4247-4254), to first determine whether prolonged incubation (24 h) of these ligands prevented NF-κB activation in response to subsequent exposure to the same ligands at higher dosage in HCECs.

TLR agonist-induced tolerance can be defined as homo-tolerance (i.e., the tolerizing and the secondary stimuli use the same TLRs) or hetero (cross)-tolerance (i.e., the tolerizing and secondary stimuli use different TLRs). Both Pam3 (10 µg/ml) and fg (250 ng/ml) induced phosphorylation and degradation of IκB-α (indicators of TLR mediated NF-κB activation) in HCECs. The NF-κB activation in response to 10 µg/ml Pam3 was greatly diminished in HUCL cells pre-exposed to 1 µg/ml Pam3 (TLR2 homo-tolerance). However, the same pretreatment did not inhibit NF-κB activation induced by 250 ng/ml fg (i.e., no TLR2/TLR5 hetero-tolerance).

Similarly, when HUCL cells were pre-exposed to 50 ng/ml fg, no significant IκB-α phosphorylation and degradation were observed in response to subsequent challenge of high dose fg (250 ng/ml) (i.e., TLR5 homo-tolerance) whereas challenge with 10 µg/ml Pam3 led to the same level of NF-κB activation in cells with or without low dose fg-pretreatment (i.e., no TLR5/TLR2 hetero-tolerance). Thus, significant TLR homo-tolerance was induced using either Pam3 or PA fg at suboptimal concentrations of the ligands. Similar results were also obtained when TNF-α production was used as a parameter for HCEC activation (see FIG. 6). Full activation by Pam3 after 24 h fg incubation suggests that fg at this concentration was not cytotoxic to HCECs.

The conclusions drawn from this Example are: i) Both TLR2 and TLR5 agonists induce self-tolerance and pretreatment of cells with low dosage of TLR agonists blunts pro-inflammatory responses that are otherwise induced by the same ligands at a higher concentration in HCECs. ii) Pam3 and fg do not induce a state of cross-tolerance in HCECs. This differs from that observed in intestinal epithelial cells where LPS and LTA induce cross hypo-responsiveness with each other (Otte, J. M., et al. 2004. *Gastroenterology* 126:1054-1070. Since both TLR2 and TLR5 share the same MyD88-

IRAK-NF-κB signaling pathway, targeting a common mediator(s) of intracellular signaling is unlikely to be an underlying mechanism.

Example 4

TLR Agonist-Induced Tolerance Dampens Hcec Inflammatory Response to Bacterial Challenge In Vitro As pretreatment of HCECs with Pam3 and fg resulted in tolerance to the subsequent challenge of the same TLR agonists, this Example was performed to determine whether low dosage of TLR agonists induces tolerance towards live bacteria in HCECs. Primary culture of HCECs (p3) were pre-treated with 1 µg/ml Pam3 and 50 ng/ml fg for 24 h and then challenged with live SA and PA for 6 h, respectively.

The amounts of TNF-α in the culture media were measured using ELISA. First, much stronger response of HCECs to PA was observed than that to SA. Pre-incubation of HCECs with Pam3 significantly attenuated SA-induced TNF-α production, about 50% reduction of TNF-α was observed in Pam3-pretreated cells, suggesting a partial inhibition of Pam3-induced tolerance to SA-challenge. Exposure to live PA resulted in a TNF-α. burst, a striking 43.6 fold increase compared with control. Pre-incubation of HCECs with 50 ng/ml fg substantially diminished, but did not completely block PA-induced TNF-α production; a 2.96 fold increase was observed in fg-pretreated and PA-challenged cells when compared with control.

Similar results were also observed in HUCL cells in several independent experiments (n=3). Fg-induced tolerance to different strains of PA was tested, and the results showed that while 10 ng/ml fg pretreatment induced significant tolerance to PA01 strain, 50 ng/ml fg was required for attenuating ATCC19660 strain-induced TNF-α production, suggesting that fg induces cross-strain tolerance in HCECs. Thus, fg-pretreatment induces HCEC tolerance to PA-challenge. This Example is believed to be unique in many aspects including the use of fg to induce epithelial tolerance, the dosage used that causes cell activation, but little cytokine production, and the observation of a muted cytokine burst induced by live bacterial stimulation in tolerant cells.

Fg was selected for further study of fg-induced HCEC tolerance because low dose fg induced significant tolerance to PA while Pam3 only partially reduced epithelial response to SA. In addition, TLR5-fg interaction is the simplest among cell surface TLRs with no co-receptors but asialoGM1 (Adamo, R., et al. 2004. Am J Respir Cell Mol Biol 30:627-634; McNamara, N., ct al. 2006. Am J Respir Cell Mol. Biol.) required for ligand-binding and only MyD88 as the adaptor protein (Akira, S., et al. 2004. Nat Rev Immunol 4:499-511) Furthermore, as the only TLR agonist as a protein, fg appears to interact only with TLR5 and exhibits minimal or no cytotoxic effects on cells (Ramos, H. C., et al. 2004. Trends Microbiol 12:509-517; Gewirtz, A. T. 2006. Curr Opin Gastroenterol 22:8-12).

Example 5

Flagellin (50 ng/ml) Induced IκB-α Phosphorylation but not IL-8 Production in HCECs To better understand the mechanism of fg-induced tolerance in HCECs, this Example was performed as a dose-dependent study. The effects of fg on NF-κB activation and cytokine production were assessed, and the results are shown in FIG. 7. NF-κB activation, judged from IκB-α phosphorylation, was detectable in cells treated with 10 ng/ml fg and was more apparent when 50 ng/ml or higher fg was used. Thus, fg at 50 ng/ml was sufficient to induce IκB-α phosphorylation, and likely NF-κB activation, within 1 h. The production of cytokines (IL-8 shown, IL-6 and TNF-α also tested) was tested. While 10 ng/ml fg essentially exhibited no effects on IL-8 production, 50 ng/ml fg stimulated a low level increase (<2 fold as compare with control) in IL-8 secretion. On the other hand, 7.1 times more IL-8 was produced by cells treated with 250 ng/ml fg. Thus, the concentration of fg used here to induce TLR5-tolerance (50 ng/ml) was sufficient to induce NF-κB activation, but not to elicit strong inflammatory response in HCECs.

It is believed in the art that disruption of the major signaling components leading to NF-κB activation is, at least in part, responsible for tolerance induction and the initial activation of NF-κB is likely to be required for tolerance phenotype. The results presented here are consistent with this mechanism. The low level of cytokine produced under this condition leads to a suitable dosage for in vivo use of fg that induces tolerance to bacterial challenge but does not elicit a significant inflammatory response. This has important clinical relevance, as induction of inflammation is an undesired effect.

Example 6

Gene Expression in Infected Cornea

Using real time RT-PCR and other genetic methods, expression is predicted as follows in Table 2.

TABLE 2

| $1^{st}$ stimulation | – | – | Fg (50 ng/ml) | Fg (50 ng/ml) |
|---|---|---|---|---|
| $2^{nd}$ stimulation | – | Fg (250 ng/ml)/PA | – | Fg (250 ng/ml)/PA |
| iNOS | – | +++ | ++ | +++ |
| hBD2 | – | ++ | + | +++ |
| LL-37 | – | ++ | + | +++ |
| Mn-SOD | – | ++ | +++ | +++ |

Production of both hBD2, LL-37, and NO (a free radical gas produced by iNOS with important signaling and antimicrobial actions) may result in the clearing of pathogens (Kumar, A., et al., 2005 Microbes Infect. 8:380-389; Hazlett, L. D., et al., 2005 Ocul Immunol Inflamm 13:279-288). Tolerance is expected to have either no effect, or to enhance TLR-activated epithelial bactericidal/static ability. The bacteristatic activity from TLR5 activated, tolerized and tolerized/rechallenged HCECs can be attributed to the measured concentrations of hBD2 (Kumar, A., et al., 2005 Microbes Infect. 8:380-389; Hazlett, L. D., et al., 2005 Ocul Immunol Inflamm 13:279-288), NO and $H_2O_2$.

In intestinal epithelial cells, LPS-induced tolerance disturbed IL-8 expression but did not significantly alter $HXA_3$-induced PMN transepithelial migration in response to invasive Salmonella typhimurium (Savidge, T., et al., 2006 Pediatric Research 59:89-05). LXA4 (a product of mouse 12/15-Lox) produced in mouse CECs has recently been linked to increased PMN infiltration and to enhance epithelial wound healing in the cornea (Gronert, K., et al., 2005 J Biol Chem 280:15267-15278). In vitro PMN migration assays reveal if tolerance compromises PMN infiltration. PMN migration induced by TLR5 activated HCECs is probably due to both IL-8 and HXA3; whereas that by tolerized/rechallenged cells is likely due to HXA3 as the expression of IL-8 in these cells is suppressed.

In vivo tolerance may dampen inflammation but not PMN infiltration at the early stage of bacterial infection due to the expression of 12-Lox. Mn-SOD is a component of the cellular antioxidant defense. Demonstration of an increase in Mn-SOD expression in tolerized and/or tolerized/rechallenged HCECs indicates a decrease in intracellular oxyradical stress occurring in infected cornea. Expression of the protective genes correlates with enhanced epithelial innate killing ability, rapid PMN infiltration induced by $HXA_3$, and facilitated epithelial wound healing as a result of cell reprogramming, and their combined action contributes to the observed immune protection in the TLR tolerized mice.

Lipoxin A(4) (LXA4), a lipid autacoids produced by mouse 12/15-Lox (functional equivalent to human 12, and 15-Lox) was found to significantly increase PMNs in the cornea while abrogating KC (a mouse homologue of human IL-8) production. LXA4 also promotes corneal re-epithelialization (Gronert, K., et al., 2005 *J Biol Chem* 280:15267-15278).

Example 7

Inhibition of Gene Expression in the Cornea

An important aspect of the tolerance phenotype is the enhanced bactericidal or bacteriostatic activity in epithelial cells. This example measures hBD2, NO and $H_2O_2$ in culture media and correlates their concentrations to the in vitro bactericidal/static activity. For genes that are up-regulated in corneal epithelial cells of fg-pretreated mice in response to PA infection, siRNA is used to block their expression in HCECs and determine their contribution to inhibiting bacterial growth in vitro. For siRNA that specifically attenuates the targeted gene expression in tolerized and/or tolerized/PA rechallenged cells, wherein the ability of culture media to inhibit bacterial growth is reduced, the target gene therefore plays a role in TLR-induced innate defense in the cornea. Mn-SOD is expected to contribute to the generation of extracellular $H_2O_2$ in TLR-activated HCECs, and SiRNA results will confirm this.

Available inhibitors are used to target three major components along the PI3K-GSK3 axis to define its role in acquiring tolerance. Other approaches, such as siRNA and expression of dominant negative mutants, are complementary approaches to the inhibitor studies. However, the results obtained with the use of PI3K, AKT and the GSK3 inhibitors are complementary to each other as they have opposite effects on the signaling pathways. GSK3 inhibitors are suitable as prophylactic and therapeutic agents for bacterial keratitis. Such GSK3 inhibitors are available (Woodgett, J. R., et ak., 2005 *Nat Immunol* 6:751-752) for epithelial reprogramming in vitro and dampening inflammation and controlling infection in vivo.

Example 8

Routes of Administration of Flagellin to Eye

The mouse model of corneal perforation of B6 mice is used in this example to define in vivo mechanisms of PA tolerance induced by fg. In this example, the minimal time and concentration of fg pretreatment required to induce maximal protection against PA infection in the cornea of B6 mice is determined. To determine whether fg-pretreatment leads to tolerance in epithelium and the whole cornea, activation of TLR-mediated signaling pathways such as NF-κB, P38 and JNK and PI3K/AKT are assessed, and expression of pro- and anti-inflammatory cytokines, and protective genes, are assayed by real-time RT-PCR, ELISA, and immunohistocytochemistry in fg-pretreated mice before and after PA challenge. The effects of fg pretreatment on PMN infiltration and bacterial clearance are also determined.

The manipulations shown to facilitate or enhance a tolerance phenotype are applied, alone or in combination with fg, to the animal model to determine their effects on corneal tolerance and on dampening infection-induced inflammation. Finally, a determination is made of whether fg administered after infection is in progress can be used as an adjunctive therapy to complement the bacterial killing effects of antibiotics such as ciprofloxacin and to synergistically down-regulate the host inflammatory response. These studies lead next to clinical trials to evaluate the therapeutic potential of using fg or tolerance regulating factors to treat bacterial keratitis, or to prevent contact lens-wearing associated bacterial infection.

Time and Amount of Fg Administration for Mice to Develop Tolerance and Protective Mechanisms Against PA Induced Corneal Perforation and Tissue Destruction.

A preliminary study was performed in 6 independent experiments (n=4 or 5 mice/group, respectively) of similar outcome, using PA strain 19660 in the B6 mouse model. Using the same approach (5 mice/group), the time, the route, and the minimal amount of fg administration required for mice to develop tolerance and protection against PA induced corneal perforation and tissue destruction in vivo are determined by scoring the PA infected corneas and examining histopathological changes in infected eyes enucleated on the day when the control corneas are perforated. At the time when control corneas are perforated (score+4), a clinical score of +2 or better for the treated corneas is considered as protective. With this standard, the following are determined:

i) Which route of fg administration is more effective and whether simultaneous subconjunctival and i.p. injections are required for the development of protection.

ii) Time required for the development of protection, fg will be administered by subconjunctival and/or i.p. injection at 24, 12, 6, 3 and 0 h before PA infection.

iii) Once the route of fg administration and time required for the development of protection are determined, different amounts of fg are administrated and the infected corneas are scored at day 1, 3, 5, up to 7.

The Mechanisms for In Vivo PA-Tolerance and Protection.

Once the optimal conditions for fg-administration to protect the cornea from PA infection are established, the underlying mechanisms for in vivo PA tolerance are assessed. The epithelium is expected to play an important role in corneal innate immunity, and fg treatment induces tolerance in the epithelium. Thus, the epithelial cells of fg-treated corneas are isolated by scraping the cells (up to the corneal/limbal border) off the corneas, dividing the cornea into two parts, the epithelia and stroma plus endothelia. For each condition, preferably at least ten mice are used at two separated times. The expression and/or production of cytokines, protective genes, and PMA adhesion molecules in epithelial cells and the rest of the corneas are assessed in fg-pretreated and PA exposed corneas by real time PCR, and/or ELISA/Western blotting as described (Huang, X., et al., 2005 *Invest Ophthalmol Vis Sci* 46:4209-4216; Thakur, A., et al., 2004 *Invest Ophthalmol V is Sci* 45:3177-3184).

From each group, one or two eyes are processed for histopathology (fixation and staining of the enucleated eye to examine epithelial integrity, wound healing, corneal thickness, inflammatory cells in the stroma and the anterior chamber) and immunohistocytochemistry (snap-frozen, cryostat section to determine the expression of the genes of interest in epithelial and infiltrated cells). The alteration of gene expression at different time points p.i. in fg-treated corneas is assessed and correlated to the clinical score and histopathological analyses. To understand the effects of fg-pretreatment on host defense, PMN infiltration into the cornea, especially at $1^{st}$ 24 h p.i., is assessed by measuring myeloperoxidase (MPO) activity and bacterial clearance assessed by quantitating viable bacteria in corneas using plate count. For measuring myeloperoxidase (MPO) activity and quantitating viable bacteria, the whole cornea is used. The events at molecular, cellular and morphological levels occurring at 0 (tolerant cornea), 3, 6, 12, 24, 48 and 72 h are studied. In initial studies, a significant difference, P=0.0002, was observed between fg-pretreated and control mice at this time point, as shown in FIG. 2. After this time, the cornea is examined as a whole as most epithelial cells are lost in the control group at day 4, 5, and 7.

Defining the Function of PI3K-AKT-GSK3 in Modulating the Inflammatory Response and Protection Against Keratitis In Vivo.

For this part of the Example, mice are divided into the following four groups:

Group 1: Control

Group 2: 0.4% of the GSK3 inhibitor LiCl to the diet for 5 days before PA challenge and mice are fed the same diet after infection.

Group 3: Intravenous administration of the GSK3 inhibitor SB216763 (25 µg/g) 2 h before PA challenge.

Group 4: GSK3 inhibitor SB216763 (25 µg/ml) topically applied to the infected corneas three times daily up to day seven or until corneas are perforated in the control group.

Clinical scores are assigned to each eye infected with PA at day 1, 3, 5, and 7. The expression of cytokine and other genes, histological and morphological alteration, PMN infiltration, and bacterial clearance in the infected corneas of these groups are assessed.

The Use of Fg and GSK3 Inhibitors as Adjuvant Therapies in Combination with Ciprofloxacin to Treat Experimental Bacterial Keratitis.

Fg, GSK3 inhibitor such as SB216763 (25 µg/ml), Ciloxan (a 0.3% solution of ciprofloxacin; Alcon), and GSK3 inhibitor (or fg)/Ciloxan are delivered topically to PA infected corneas (Thakur, A., et al., 2004 Invest Ophthalmol V is Sci 45:3177-3184). In this situation, since the epithelial barrier is compromised, topical application of inhibitors is expected to be effective. Therapy is initiated at 18, 24, 36, 48 and 72 h after bacterial inoculation and applied three times daily after initiation. A clinical score is assigned to each infected cornea daily up to seven days p.i. Histopathological analysis of the corneas processed at day 1, 2, or 4 after therapy initiated may be performed.

By altering the routes (subconjuctival vs. i.p. injections), the time and the amount of fg administration, the optimal efficacy of fg-treatment and the time to initiate treatment related to the time of bacterial inoculation, are established. If both routes are effective, subconjunctival injection is used for the study as it is local, more reliable than topical regarding the amount delivered, and a routinely used procedure in the Ophthalmologist's office.

A key for utilizing tolerance as anti-inflammatory therapy is to decrease inflammation without excessively compromising host defense. In initial studies, better clinical scores were observed at day 3 and day 5 p.i. in fg-pretreated corneas than that in the control, and the average score over five days period did not change significantly, suggesting the host defense is likely to be functional. This requires not only inflammation attenuated but also bacterial multiplication limited or eliminated. Bacterial clearance in the B6 model likely resulted from both epithelial innate killing and PMN infiltration. In confirmation, noticeable infiltration of PMN in fg-pretreated corneas was observed.

In fg-pretreated, PA-infected mouse corneal epithelial cells, compared with PA-infected control, other expected results are greatly attenuated expression of pro-inflammatory cytokines (IL-6 and TNF-α, and IL-1β, chemokines (MIP-2, and KC), and TH1 type/related cytokines (IFN-γ, IL-12, IL-18), and an increase in the expression of 12/15-Lox (Gronert, K., et al., 2005 J Biol Chem 280:15267-15278), TGF-β, IL-10, and IL-4 (the latter two are TH2 cytokine). The expression of MIP-2, KC (mouse homologues of human IL-8), and 12/15-Lox in fg-pretreated corneas when challenged with PA are particularly relevant, as these relate to uncompromised host defense and PMN infiltration in tolerized corneas.

Elevated PI3K-AKT signaling pathways are expected in tolerized cells, whereas NF-κB activation in response to PA infection is minimal or not expected to be observed. These are determined by Western blotting of epithelial cell extracts (AKT and IκB-α phosphorylation) and by immunohistocytochemistry (phospho-AKT staining for PI3k/AKT activation and p65 nuclear localization for NF-κB translocation).

Elevated expression of ICAM, iNOS, and/or Mn-SOD. ICAM may contribute to PMN infiltration and adhesion, iNOS to the enhanced innate defense, and Mn-SOD to the resistance to oxidative cell damage and restoration of homeostasis of the cornea. As shown in FIG. 9, corneal epithelial cells were pretreated with 50 ng/ml flagellin for 24 and then challenged with P. aeruginosa. At the indicated times, cells were processed for semi-quantitative RT-PCR to assess mRNA expression of antimicrobial peptides (human beta-defensin 2, LL-37, iNOS-to produce NO—, and S100A7. Flagellin pretreatment either had not effects or augmented the expression of antimicrobial genes while blocking P. aeruginosa-induced IL-8 and TNF-α expression in human corneal epithelial cells. If these changes are observed in vivo, this is evidence that the same mechanisms identified in vitro also exist in vivo, and that the epithelium modulates the corneal response to infection by acting either as a pro-inflammatory "sensor/amplifier" or anti-inflammatory "insulator/dampener". Pre-exposure of the cells to fg induced tolerance in epithelial cells, resulting in suppressing the pro-inflammatory "amplifier" function but promoting the anti-inflammatory "dampener" function.

For the whole corneas, the following observations are expected in fg-pretreated, PA-infected mouse cornea, compared with PA-infected control (no fg pretreatment):

Morphologically, the epithelium will be intact and fully attached to the stroma, minimal or no anterior chamber infiltration, and minimal or no corneal thinning; whereas in control mice a heavy infiltrate in the stroma with complete destruction of the epithelium and anterior part of the central stroma, and severe anterior chamber infiltration are expected.

Enhanced or unchanged PMN infiltration in infected corneas at the early phase. This may last up to three days; thereafter the infiltration is likely to be decreased. In the control, the infiltration may continuously increase.

Increased bacterial clearance. In the early phase of infection, significantly reduced number of bacteria are expected in fg-pretreated mice within first 12 to 24 h, most likely due to enhanced antimicrobial activity in epithelial cells and the infiltrated PMNs.

The expression of iNOS as well as nitrotyrosine staining will likely be the same or even higher in fg-pretreated, PA-infected corneas in both epithelial cells and PMNs) than that in control corneas.

Demonstration of unaltered or even enhanced infiltration and bacterial clearance will suggest that the sensor function of the epithelium is still functional. However, because of reduced inflammation, the outcome of the disease is expected to be much improved in fg-pretreated mice. The observed 12-Lox up-regulation in fg-treated CECs may contribute to PMN infiltration; and iNOS up-regulation probably in both epithelial and infiltrated cells, which leads to NO production, may contribute to bacterial killing/stasis in PA infected corneas; up-regulation of Mn-SOD may greatly reduce the damage caused by bacterial factors and enhance epithelial wound healing. Taken together, the in vivo studies of this Example are expected to support the in vitro mechanistic studies of TLR function in corneal epithelium and provide a basis for the utilization of TLR tolerance as a therapeutic means to treat corneal infection and inflammation.

The foregoing specification, including the specific embodiments and examples, is intended to be illustrative of the present invention and is not to be taken as limiting. Numerous other variations and modifications can be effected without departing from the true spirit and scope of the invention. All patents, patent publications, and non-patent publications cited are incorporated by reference herein.

What is claimed is:

1. A method of inducing immune tolerance to reduce local inflammation caused by an infective gram-negative bacteria in a subject to alleviate a disease or condition of the eye or the lung caused by the infective gram-negative bacteria, the method comprising locally administering to the epithelial cells of the eye or the lung of the subject an amount of a bacterial flagellin polypeptide wherein said amount is effective to induce immune self-tolerance to flagellin and immune tolerance to the infective gram-negative bacteria, and reduce local inflammation caused by the infective gram-negative bacteria in the subject.

2. The method of claim 1 wherein the disease or condition is selected from the group consisting of a corneal epithelial infection, and a lung epithelial infection.

3. The method of claim 2 wherein the gram negative bacterium is *Pseudomonas aeruginosa.*

4. The method of claim 3, wherein the local administration is to the lung and the disease or condition is cystic fibrosis.

5. The method of claim 1, wherein said flagellin polypeptide limits or eliminates multiplication of the gram-negative bacteria.

6. The method of claim 5, wherein the local administration is to the eye and the disease or condition is bacterial keratitis.

7. The method of claim 5, wherein the local administration is to the eye, the disease or condition is bacterial keratitis and the infective gram-negative bacteria is *Pseudomonas aeruginosa.*

8. The method of claim 5, wherein the disease or condition is a pulmonary infection.

9. The method of claim 5, wherein the disease or condition is selected from the group consisting of asthma, chronic obstructive pulmonary disease, and cystic fibrosis.

* * * * *